United States Patent [19]

Makino et al.

[11] Patent Number: 5,739,165
[45] Date of Patent: Apr. 14, 1998

[54] STABILIZED SOLID PHARMACEUTICAL PREPARATION AND METHOD OF PRODUCING THE SAME

[75] Inventors: Tadashi Makino; Yoshio Mizukami; Jun-Ichi Kikuta, all of Osaka, Japan

[73] Assignee: Takeda Chemical Industries, Ltd., Osaka, Japan

[21] Appl. No.: 278,701

[22] Filed: Jul. 15, 1994

Related U.S. Application Data

[63] Continuation of Ser. No. 45,867, Apr. 15, 1993, abandoned.

[30] Foreign Application Priority Data

Apr. 17, 1992 [JP] Japan .................. 4-098169
Apr. 7, 1993 [JP] Japan .................. 5-106167

[51] Int. Cl.$^6$ .......................... A61K 31/19; A61K 31/135
[52] U.S. Cl. ............................ 514/570; 514/653
[58] Field of Search ........................ 514/570, 653

[56] References Cited

U.S. PATENT DOCUMENTS 5,025,019  6/1991  Sunshine et al. ................. 514/277

FOREIGN PATENT DOCUMENTS 0 159 852  10/1985  European Pat. Off. .
0 348 683  1/1990  European Pat. Off. .
0 396 404  11/1990  European Pat. Off. .
WO85/04589  10/1985  WIPO .
WO91/17746  11/1991  WIPO .

OTHER PUBLICATIONS

Dittert, Sprowls' American Pharmacy, Seventh Edition, p. 334, 1985.

Primary Examiner—William R. A. Jarvis
Attorney, Agent, or Firm—Wenderoth, Lind & Ponack

[57] ABSTRACT

A solid pharmaceutical preparation containing 5 to 50% by weight of ibuprofen and 0.1 to 10% by weight of phenylpropionamide or a pharmaceutically acceptable salt thereof which are stabilized. The solid pharmaceutical preparation can be produced by means of granulating with carriers at least one active ingredient, preferably both ingredients separately into the ibuprofen group and the phenylpropanolamine group, and mixing the former with the latter to enhance the stability of the active ingredients. Preferably, in the phenylpropanolamine group, the amount of any reducing sugar is minimized to such an extent as to maintain the stability of the active ingredient. The above pharmaceutical preparation is suitable for a cold remedy, which has a more excellent pharmacological activity based on ibuprofen, less decomposability of phenylpropanolamine and less change of external appearance of the preparation due to low compatibility between phenylpropanolamine and ibuprofen. Therefore, the pharmaceutical preparation has a longer period of quality assurance.

19 Claims, No Drawings

STABILIZED SOLID PHARMACEUTICAL PREPARATION AND METHOD OF PRODUCING THE SAME

This application is a continuation of application Ser. No. 08/045,867, filed Apr. 15, 1993, now abandoned.

FIELD OF THE INVENTION

The present invention relates to a stabilized solid pharmaceutical preparation comprising ibuprofen which is utilized as a antipyretic, analgesic and/or antiinflammatory agent, phenylpropanolamine or a salt thereof which is effective for nasal mucus and nasal congestion, and if desired, other active ingredients, and to a method of producing the same. Particularly, this invention relates to a solid pharmaceutical composition comprising the ingredient group containing ibuprofen (hereinafter referred to as "ibuprofen group") and the ingredient group containing phenylpropanolamine or a salt thereof (hereinafter referred to as "phenylpropanolamine group") in a form which inhibits the contact of the ingredients, and to a method of producing the same.

BACKGROUND OF THE INVENTION

Ibuprofen was first synthesized by Nicholson and Adamo in 1964, developed as a drug by Boots Pure Drug Co. Ltd. in England and has been utilized mainly as an antipyretic, analgesic and/or antiinflammatory agent. On the Other hand, phenylpropanolamine hydrochloride is a sympathomimetic drug having ephedrine-like pharmacological activities and therapeutic activities for nasal mucus and nasal congestion, and utilized as a drug of rhinitis in nonproprietary drugs.

In JP-A-61-501913 corresponding to WO85/04589, there is disclosed a pharmaceutical composition of cold remedy comprising nonsteroidal antiinflammatory agents such as ibuprofen and the like as an analgesic ingredient and phenylpropanolamine hydrochloride as an anti-congestion ingredient. In WO91/17746, there is disclosed an oral drug containing ibuprofen, phenylpropanolamine hydrochloride and carriers. These pharmaceutical preparations are prepared by mixing ibuprofen and phenylpropanolamine hydrochloride directly with lactose and other carriers.

As a result of various investigations for preparing complex cold remedies having more excellent action, the present inventors also found that pharmaceutical preparations comprising ibuprofen generally used as an antipyretic, analgesic and/or antiinflammatory agent and phenylpropanolamine or a salt thereof (e.g. phenylpropanolamine hydrochloride, etc.) are favorable as cold remedies above all.

These pharmaceutical preparations, however, lower the drug stability of the active ingredients, and, thus, cause not only decrease of the effective amount of the ingredients, but also change of external appearance during the course of time.

In more detail, since ibuprofen has a lower melting point of 75° C., when ibuprofen is in contact with other ingredients, it may frequently cause melting point depression of the other ingredients. Furthermore, pharmaceutical compositions comprising ibuprofen and other ingredients have low drug stability, thus it is liable to cause inactivation of active ingredients, change of external appearance and so on. "Incompatibility of ibuprofen granules" [Sato, Pharmacy, 27, 12, 73–78, (1976)] discloses that ibuprofen is incompatible with methylephedrine or sodium bicarbonate, and "Researches for incompatibility of pharmaceutical preparations" [Ueda, Report of Pharmacological Research Institute of Toyama Pref., Vol. 1984/1985, p 127–234, (1987)] discloses that ibuprofen is incompatible with dl-chlor-Pheniramine maleate, ascorbic acid and so on.

On the other hand, it is confirmed that decomposition of phenylpropanolamine hydrochloride is promoted by the reaction with some kinds of sugars, and by pH variation of a solution [R. H. Barry., J. Pharm. Sci. 71, No. 1, January 116–118, (1982)]. "Researches for incompatibility of pharmaceutical preparations" [Ueda, Report of Pharmacological Research Institute of Toyama Pref., Vol. 1984/1985, p 127–234, (1987)] discloses that phenylpropanolamine hydrochloride is incompatible with lysozyme chloride, potassium guaiacolsulfonate, dextromethorphan hydrobromide and so on.

Such problems as described above are particularly remarkable in a pharmaceutical preparation containing both ibuprofen and phenylpropanolamine or a salt thereof. For example, in a pharmaceutical preparation containing ibuprofen and phenylpropanolamine hydrochloride, the stability of the later ingredient with the passage of time is particularly low under the condition of high temperature and high humidity, and change of external appearance due to low compatibility with ibuprofen is visible. Therefore, among pharmaceutical preparations containing ibuprofen and phenylpropanolamine or a salt thereof, no successfully stabilized pharmaceutical preparations having adequate utility have been developed yet.

SUMMARY OF THE INVENTION

Accordingly, it is an object of the present invention to provide a solid pharmaceutical preparation containing both ibuprofen and phenylpropanolamine or a pharmaceutically acceptable salt thereof, in which the active ingredients are stabilized, and a method of producing such a pharmaceutical preparation.

It is another object of the invention to provide a solid pharmaceutical preparation in which inactivity of phenylpropanolamine or a pharmaceutically acceptable salt thereof and change of external appearance of the pharmaceutical preparation with the passage of time are remarkably suppressed, and thus longer quality assurance period and higher quality of products are obtained, and to provide a method of producing such a pharmaceutical preparation.

It is a further object of the invention to provide a solid pharmaceutical preparation useful as a cold remedy such as a general cold remedy and the like and to provide a method of producing the same.

As a result of intensive investigations for stabilization of pharmaceutical preparations comprising ibuprofen and phenylpropanolamine or a salt thereof, the inventors of the present invention found that when the ibuprofen group and phenylpropanolamine group are prepared separately, the stability of the active ingredients is enhanced remarkably, and that when the phenylpropanolamine group does not contain a large quantity of specific carriers, inactivation of the active ingredients is remarkably suppressed and a stabilized pharmaceutical preparation is thus obtained. The present invention has been accomplished based on these findings and further studies.

Thus, the present invention provides a stabilized solid pharmaceutical preparation containing ibuprofen and phenylpropanolamine or a pharmaceutically acceptable salt thereof. In this pharmaceutical preparation, ibuprofen and phenylpropanolamine or a pharmaceutically acceptable salt thereof (e.g. phenylpropanolamine hydrochloride, etc.) may be contained separately. Further, the phenylpropanolamine group containing phenylpropanolamine or a pharmaceutically acceptable salt thereof may include some amount of reducing sugars unless they harm the drug stability.

The present invention further provides a method of producing a stabilized solid pharmaceutical preparation which comprises granulating at least one ingredient from between ibuprofen and phenylpropanolamine or a pharmaceutically acceptable salt thereof with carriers, and mixing the granulated preparation with the other ingredient. This method may include the steps of preparing "granulated preparation" containing ibuprofen group and "granulated preparation" containing phenylpropanolamine and mixing both of the granulated preparations.

DETAILED DESCRIPTION OF THE INVENTION

In this specification, the term "separately" in "grouping and containing separately" refers to any and all cases in which the ibuprofen group and the phenylpropanolamine group are contained in a form which inhibits the contact of the ingredients. The term "ibuprofen group" means a group containing ibuprofen. The term "phenylpropanolamine group" means a group containing phenylpropanolamine or a pharmaceutically acceptable salt thereof. The term "granulated preparation" means preparations including fine granules, granules and pills and the like.

Typical examples of the solid pharmaceutical preparation include solid pharmaceutical preparations for oral administration such as granulated preparations (for example, fine granules, granules and pills and the like), tablets, capsules and so on. The pharmaceutical preparation of the present invention is suitable for a cold remedy among others.

The solid pharmaceutical preparation of the present invention contains, as active ingredients, ibuprofen and phenylpropanolamine or a pharmaceutically acceptable salt thereof. Examples of salts of phenylpropanolamine include any salts which may be pharmacologically acceptable, for example, phenylpropanolamine hydrochloride and the like.

The pharmaceutical preparation of the present invention may contain, if desired, active ingredients other than ibuprofen and phenylpropanolamine or a pharmaceutically acceptable salt thereof. These active ingredients include, for example, antipyretic, analgesic and/or antiinflammatory agents, antiussive and/or expectorants, bronchodilators, Chinese medicinal extracts, vitamins, gastric antacids and mucosa-protecting agents, minerals, amino acids and so on.

As the antipyretic, analgesic and/or antiinflammatory agents, there may be mentioned, for example, acetoaminophen, phenacetin, aspirin, ethenzamide, aminopirin, phenylbutazone, ketophenylbutazone, indomethacin, naproxen, ibufenac, serratiopeptidase, lysozyme chloride, mefenamic acid and so on.

Examples of the antiussive and/or expectorants include chloperastine hydrochloride, codeines such as dihydrocodeine phosphate and codeine phosphate, oxymetebanol, eprazinone hydrochloride, dextromethorphan or a salt thereof (e.g. dextromethorphan hydrobromide, etc.), tipepidine, ephedrine hydrochloride, dl-methylephedrine hydrochloride, noscapine, dimemorfan or a salt thereof (e.g. dimemorfan phosphate, dimemorfan sulfate, etc.), bromhexine hydrochloride and so on.

The bronchodilators include caffeine anhydride, ephedrine, theophylline, diphenhydramine or a salt thereof (e.g. diphenhydramine hydrochloride, etc.), chlorpheniramine or a salt thereof (e.g. chlorpheniramine D-maleate, etc.) and so on.

Examples of the Chinese medicinal extract include an extract from Gylcyrrhizae radix, Polygala senega, Bupleuri radix, Cinnamomi cortex, Pherariae radix, Ephedrae herba, Schizpnepetae herba, Forsythiae fructus, Armeniacae semen, Pinellae tuber, Paeoniae radix, Asiasri radix, Zingiberis phizoma, Schisandrae fructus, Perillae herba, Ginseng radix, Aurantii nobilis pericarpium and the like.

As examples of vitamins, there may be mentioned vitamin $B_1$ (e.g. fursultiamine, etc.), vitamin $B_2$, vitamin C and so on.

Gastric antacids and mucosa-protecting agents include magnesium hydroxide, magnesium oxide, aluminium hydroxide, aluminium sulfate, magnesium metasilicate aluminate [e.g. Neusilin (Trade name)], magnesium silicate aluminate, synthetic hydrotalcite [e.g. ALCAMAC (Trade name)], coprecipitate of aluminium hydroxide and sodium bicarbonate [e.g. Kumulite (Trade name)], sucralfate and the like. Where the pharmaceutical preparations of the present invention are utilized as cold remedies, these active ingredients are mixed usually in accordance with a standard for cold remedy described in Drug Manufacturing Standard (revised in 1991, Yakugyo Jihosha Co., Ltd., Japan).

According to the solid pharmaceutical preparation of the present invention, ibuprofen and phenylpropanolamine or a pharmaceutically acceptable salt thereof are stabilized in the preparation. Excellent stability of the ingredients can be achieved by means of grouping and containing separately ibuprofen and phenylpropanolamine or a pharmaceutically acceptable salt thereof. In this case, the contact of ibuprofen and phenylpropanolamine or a pharmaceutically acceptable salt thereof is inhibited by a carrier interposed between them.

Furthermore, the solid pharmaceutical preparation containing the ibuprofen group and the phenylpropanolamine group separately, has an advantage in that incompatible ingredients can be utilized without harming the stability of the active ingredients. For example, dl-methylephedrine hydrochloride, vitamin C, sodium bicarbonate etc. which are incompatible with ibuprofen can be contained in the phenylpropanolamine group, and lysozyme hydrochloride which is incompatible with phenylpropanolamine can be contained in the ibuprofen group.

As the carriers, unless contrary to the objects of the invention and harm the stability of the active ingredients, various conventional additives used in the manufacture of solid pharmaceutical preparations, particularly granulated preparations may be employed. The additives mentioned just above include various excipients such as lactose, powder sugar, mannitol, corn starch, talc, crystalline cellulose [e.g. Avicel (Trade name) etc.], magnesium stearate, light silicic anhydride, magnesium carbonate, calcium carbonate, L-cysteine, etc.; binders such as starch, alpha-starch, gelatin, powdered gum arabic, methylcellulose, carboxymethylcellulose, carboxymethylcellulose sodium, hydroxypropylcellulose (hereinafter referred to as HPC), hydroxypropylmethylcellulose, polyvinylpyrrolidone, pullulan, dextrin, etc.; disintegrators such as carboxymethylcellulose calcium [croscarmellose calcium, e.g. ECG505 (Trade name)], low-substituted hydroxypropylcellulose (hereinafter referred to as L-HPC), croscarmellose sodium [e.g. Acdisol (Trade name)], etc.; surfactants including anionic surfactants such as sodium alkylsulfates etc. and nonionic surfactants such as polyoxyethylene-sorbitan fatty acid esters, polyoxyethylene-fatty acid esters and polyoxyethylene-castor oil derivatives, etc.; colorants; corrigents; adsorbents; preservatives; wetting agents; antistatic agents; disintegration retarders; and so on.

Among these carriers, at least excipients and binders are frequently utilized, as well as disintegrators.

Lipids may be used, if necessary, in the preparation. Examples of such lipids include hydrogenated oils derived from fats and oils such as castor oil, cottonseed oil, soybean oil, rapeseed oil, beef tallow, etc.; beewax, carnauba wax, lecithin, paraffin, microcrystalline wax; fatty acids such as stearic acid and palmitic acid, and fatty acid salts such as sodium and potassium salts; fatty alcohols such as stearyl alcohol and cetyl alcohol; glycerides such as glycerol tristearate, polyglycerol fatty acid esters and the like.

In the preferred embodiments, at least one ingredient selected form ibuprofen and phenylpropanolamine or a pharmaceutically acceptable salt thereof is contained in granulated preparations which are granulated with carriers. In this case, the other group of the ingredient ungranulated may be mixed with the granulated group.

Typically preferred embodiments include a solid preparation in which ibuprofen and phenylpropanolamine or a pharmaceutically acceptable salt thereof are grouped and contained separately in different granulated preparations. In this case, the solid pharmaceutical preparation can be produced by means of mixing the granulated preparations of ibuprofen and the granulated preparations of phenylpropanolamine or a pharmaceutically acceptable salt thereof.

The preferred methods for "grouping and containing separately" include (1) a process of granulating the said active ingredients separately in different granulated preparations, and mixing the preparations so as to lessen contact area of the said active ingredients, (2) a process of molding a mixture of the granulated preparation of the ibuprofen group and the granulated preparation of the phenylpropanolamine group into tablets, (3) a process of molding the granulated preparation of the ibuprofen group and the granulated preparation of the phenylpropanolamine group into tablets having two or more layers using a multilayer tablet machine (for example, a machine manufactured by Kikusui Seisakusho Co. Ltd., etc.), in which each different adjacent layer contains a different group, (4) a process of molding the granulated preparation of the ibuprofen group and the granulated preparation of the phenylpropanolamine group into sandwich-type tablets having multiple layers, in which each different adjacent layer contains different group and, between each layer, comprise thin buffering layers, and (5) a process of coating or encapsulating as microcapsules at least one group of the active ingredients with a polymer, thereby separating each other so as to stabilize the active ingredients.

As typically preferred embodiments of such methods for preparation, there may be mentioned as follows.

Namely, for "grouping and containing separately", the ibuprofen group can be prepared by mixing ibuprofen, and if necessary, other drugs, and carriers, preferably at least a binder and an excipient, and granulating the mixture in accordance with a conventional manner. When wet fluidized-bed granulation is used, for example, the granulated preparations containing the ibuprofen group may be produced by mixing and charging suitable amount of additives such as excipients, disintegrators and the like, ibuprofen, and if desired, other drugs, into a fluidized-bed granulator, spraying a binder such as an aqueous solution of hydroxypropylcellulose and the like into the granulator, and drying the granulation product to give the solid granulated preparation.

In the granulated ibuprofen group, the proportion of ibuprofen is, for example, 10 to 60% by weight, preferably 20 to 40% by weight, based on the total weight of the ibuprofen group. The ibuprofen group usually contains as other ingredients 0 to 10% by weight, preferably 0 to 5% by weight of other drugs, 30 to 90% by weight, preferably 50 to 80% by weight of carriers such as 0.5 to 15% by weight, preferably 1 to 10% by weight of binder, 20 to 85% by weight, preferably 40 to 75% by weight of excipient, 0.5 to 15% by weight, preferably 1 to 10% by weight of disintegrator, based on the total weight of the ibuprofen group.

The phenylpropanolamine group may be prepared in the same manner as mentioned in the ibuprofen group, except utilizing the phenylpropanolamine or a pharmaceutically acceptable salt thereof instead of ibuprofen. For example, when wet fluidized-bed granulation is used, the granulated preparation of the phenylpropanolamine group may be produced by mixing and charging suitable amount of additives such as excipients, disintegrators, and the like, phenylpropanolamine or a pharmaceutically acceptable salt thereof, and if desired, other drugs into a fluidized-bed granulator, spraying a binder such as HPC and so on into the granulator, and drying the granulated product to give the solid granulated preparation.

When the phenylpropanolamine group contains a large quantity of a reducing sugar such as lactose, sucrose and the like, the stability of phenylpropanolamine or its salt is harmed. Therefore, preferably, the amount of any reducing sugar contained in the phenylpropanolamine group is minimized to such an extent as to maintain the stability of phenylpropanolamine or its salt. Typical examples of the preferred include (1) the phenylpropanolamine group which does not contain a reducing sugar, (2) the phenylpropanolamine group where even if it contains a reducing sugar, the reducing sugar should be contained in a proportion of 5% by weight or less, preferably 3% by weight or less relative to the whole weight of granulated preparation of the phenylpropanolamine group, and (3) the phenylpropanolamine group which contains a sugar alcohol which does not have a reducing hydroxyl group, such as mannit, maltitol, sorbitol, etc. instead of such a reducing sugar.

In the granulated phenylpropanolamine group, the content of phenylpropanolamine e or a pharmaceutically acceptable salt thereof is, for example, 10 to 60% by weight, preferably 20 to 40% by weight, on the base of the total amount of the phenylpropanolamine group. The phenylpropanolamine group usually contains, as other ingredients, 0 to 50% by weight, preferably 0 to 40% by weight of other drugs and 20 to 90% by weight, preferably 30 to 70% by weight of carriers such as 0.5 to 15% by weight, preferably 1 to 10% by weight of binder, 20 to 70% by weight, preferably 30 to 60% by weight of excipient, and 0 to 15% by weight, preferably 0 to 10% by weight of disintegrator.

The granulated preparation may be prepared by use of conventional granulation method. As examples of such methods, there may be mentioned wet granulation such as spray granulation, spray centrifugal granulation and the like, using a solution or a suspension such as water, an organic solvent and so on and dry granulation such as fluidized bed granulation, centrifugal granulation and the like, using powdery or granular binders.

The solid preparation according to the present invention may be provided in a variety of dosage forms such as fine granules, granules, pills, tablets obtainable by compression-molding the fine granules or granules, and capsules obtainable by filling capsules with the fine granules or granules. The mean particle size of the fine granules may be, for example, about 10 to 500 µm, preferably about 100 to 500 µm. The mean particle size of the granules may be, for example, about 500 to 1500 µm.

The solid pharmaceutical preparations including fine granules, granules and pills can be manufactured by blending the granulated preparation of the ibuprofen group and the granulated preparation of the phenylpropanolamine and filling divided packages with the mixture. Capsules can be produced by means of blending the granulated preparation of the ibuprofen group and the granulated preparation of the phenylpropanolamine group and filling capsules with the mixture directly using capsule-filling machine, as well as by means of filling capsules with said two kinds of granulated preparations in the form of two layers where each adjacent layer contains different granulated preparation respectively.

Tablets can be prepared by means of blending the granulated preparation of the ibuprofen group, the granulated preparation of the phenylpropanolamine group, carriers (e.g. excipients, binders, disintegrators, etc.) and so on, and compression-molding the mixture.

In preparations as described above, the ibuprofen group and the phenylpropanolamine group can be mixed in a suitable ratio, depending on the proportion of the active ingredients in each group, for example, about 2 to 98 of the former: 98 to 2 of the latter (by weight), preferably about 5 to 95 of the former: 95 to 5 of the latter (by weight).

Where the pharmaceutical preparation of the present invention is used as a remedy for cold, the contents of ibuprofen in the ibuprofen group may be in a proportion of about 50 to 90% by weight, preferably about 60 to 80% by weight of the pharmaceutically commonly used amount of ibuprofen which is contained alone as active ingredient. The preparation is preferred to contain ibuprofen, depending on the type of the preparation, in such a proportion as the dosage of ibuprofen may range about 100 to 1000 mg per day, preferably about 200 to 700 mg per day, and more preferably about 300 to 500 mg per day. The preparation contains the phenylpropanolamine group in such a proportion as the dosage of phenylpropanolamine or a pharmaceutically acceptable salt thereof may range about 10 to 200 mg per day, and preferably about 30 to 100 mg per day.

The solid pharmaceutical preparation such as tablets contains ibuprofen in a proportion of 5 to 50% by weight, preferably 10 to 30% by weight, phenylpropanolamine or a pharmaceutically acceptable salt thereof in a proportion of 0.1 to 10% by weight, preferably 1 to 5% by weight, based on the total weight of the preparation. The solid pharmaceutical preparation usually contains about 0 to 20% by weight, and preferably about 1 to 15% by weight of other active ingredients and 40 to 95% by weight, preferably about 50 to 90% by weight of carriers; and as such carriers, about 0.1 to 10% by weight, and preferably 0.5 to 5% by weight of binders, about 30 to 80% by weight, and preferably about 40 to 80% by weight of excipients and about 1 to 15% by weight, and preferably about 3 to 10% by weight of disintegrators may be contained, on the base of the total weight of the solid pharmaceutical preparation.

In order to stabilize the active ingredients, the content of water in the whole pharmaceutical is, preferably, controlled. As to the preferred content of water in the solid pharmaceutical preparation, the percentage of less-on-drying (LOD) is in the range of 4% or less , preferably in the range of 3.5% or less and the equilibrium relative humidity is in the range of 33% or less.

The pharmaceutical preparation of the present invention may be a coated preparation in which the granulated preparation such as fine granules, granules, pills and the like or tablets is coated with a coating composition. The coating composition includes, for example, hydroxypropylmethylcellulose, hydroxypropylcellulose, methylcellulose, ethylcellulose, polyvinylpyrrolidone, hydroxypropylmethylcellulose phthalate, hydroxypropylmethylcellulose acetate succinate, carboxymethylethylcellulose, cellulose acetate trimellitate, cellulose acetate phthalate, aminoalkyl methacrylate copolymer, acrylic acid copolymer, methacrylic acid copolymer, polyvinyl acetate phthalate, methacrylic acid-methyl methacrylate copolymer and so on.

In the coating procedure, coating auxiliaries may be used in accordance with the conventional manner. As such coating auxiliaries, there may be mentioned, for example, polyethylene glycol 6000, polysorbate (e.g. Tween 80, etc.), surfactants, colorants such as titanium oxide, red oxide and so on.

The coating amount of the coating composition can be selected according to the type of solid preparation. The coating amount relative to the solid preparation is about 0.1 to 30% by weight, and preferably about 0.5 to 10% by weight for tablets, about 0.1 to 50% by weight, and preferably about 1 to 20% by weight for pills and granules, and about 0.1 to 100% by weight, and preferably about 1 to 50% by weight for fine granules.

Coating can be carried out by the conventional manner, such as pan coating, air-suspension or fluidized bed coating, centrifugal coating and so on. When the coating composition is a solution or dispersion containing water or an organic solvent, the spray-coating method can also be employed. The proportion of such water or organic solvent may for example be about 25 to 99% by weight. The type of organic solvent is not so critical. Thus, for example, alcohols such as methanol, ethanol, isopropyl alcohol, etc.; ketones such as acetone etc.; and halogenated hydrocarbons such as chloroform, dichloromethane, trichloroethane, etc. can be employed. The typically preferred examples of the solvent include water and/or alcohols, and among them, specifically preferred is water.

Thus the solid pharmaceutical preparation of the present invention is a stabilized pharmaceutical preparation wherein decomposition of the active ingredients with the passage of time is controlled. When the solid pharmaceutical preparation of the present invention is used for the therapy of cold as a common cold remedy which includes general cold remedy for mammals such as human beings, the solid pharmaceutical preparation such as tablets, granules, capsules, and the like, may be administered orally by the conventional manner.

The following examples and comparative example are merely intended to illustrate the present invention in further detail and should not be construed as defining the scope of the invention.

EXAMPLES

Examples 1 to 3 and Comparative Example 1

Using a fluidized-bed granulator (FD-5S, manufactured by Powrex Co., Ltd., Japan), granules of the ibuprofen group (hereinafter briefly referred to as "group I") and granules of the phenylpropanolamine group (hereinafter briefly referred to as "group P") were prepared in accordance with the formulation indicated in Table 1. The group I and the group P were prepared respectively by spraying an aqueous solution of HPC as a binder for granulation, drying and comminuting the resulting granulation product to give granules.

To the granules of the group I and the granules of the group P thus obtained were added crystalline cellulose, croscarmellose sodium (Acdisol) and magnesium stearate in the ratio indicated in Table 1, and the mixture was compression-molded with a tablet machine (Correct 19K, Kikusui Seisakusho Co., Ltd., Japan) with an oblong punch (13.5 mm×6.2 mm) at a molding pressure of 2 ton/cm$^2$ to provide (weight: 400 mg) tablets.

In Example 2, tablets were prepared by use of mannit in the group P, and in Example 3, tablets were prepared by use of lactose in the group P.

In Comparative Example 1 as a control, all components corresponding to those of Example 1 except the aqueous solution of HPC were mixed simultaneously, then the aqueous solution of HPC was sprayed for granulation and the resulting granulation product was dried and comminuted to provide granules. To the granules thus obtained were added crystalline cellulose, croscarmellose sodium (Acdisol) and magnesium stearate, and the mixture was compression-molded to give tablets.

TABLE 1

| Ingredient (mg) | Example 1 Group I | Example 1 Group P | Example 2 Group I | Example 2 Group P | Example 3 Group I | Example 3 Group P | Comparative Example 1 |
|---|---|---|---|---|---|---|---|
| Ibuprofen | 450 | | 450 | | 450 | | 450 |
| Dihydrocodeine phosphate | 24 | | 24 | | 24 | | 24 |
| Phenylpropanolamine hydrochloride | | 75 | | 75 | | 75 | 75 |
| Caffein anhydride | | 75 | | 75 | | 75 | 75 |
| Chlorphenimamine maleate | | 7.5 | | 7.5 | | 7.5 | 7.5 |
| Lactose | 955.5 | | 645 | | 645 | 310.5 | 955.5 |
| Mannit | | | | 310.5 | | | |
| Corn starch | 216 | 114 | 216 | 114 | 216 | 114 | 330 |
| Acdisol | 60 | | 60 | | 60 | | 60 |
| HPC | 54.5 | 8.5 | 45 | 18 | 45 | 18 | 63 |
| (Water) | (1036 μl) | (162 μl) | (855 μl) | (342 μl) | (855 μl) | (342 μl) | (1197 μl) |
| Subtotal | 1760 | 280 | 1440 | 600 | 1440 | 600 | 2040 |
| Crystalline cellulose | 254 | | 254 | | 254 | | 254 |
| Acdisol | 96 | | 96 | | 96 | | 96 |
| Magnesium stearate | 10 | | 10 | | 10 | | 10 |
| Total | 2400 | | 2400 | | 2400 | | 2400 |
| Content of water | 3.1% | | 3.0% | | 2.9% | | 2.7% |

The tablets obtained in Examples 1 to 3 and Comparative Example 1 were stored at 40° C. or 50° C. for the respective intervals given in Table 2, then assayed for the drug (phenylpropanolamine) by liquid chromatography, and the change of external appearance of the preparations was also observed. The results are shown in Table 2. In the table, each value indicates the percent by weight drug residue remaining at the time of assay, the phenylpropanolamine content of the tablets immediately after manufacture being taken as 100%. The results shown in Table 2 indicate that the solid pharmaceutical preparation of the present invention is superior in stability of phenylpropanolamine and has less change of the external appearance relative to the preparation of Comparative Example 1.

TABLE 2

| Storage temperature | Storage period | | Example 1 | Example 2 | Example 3 | Comparative Example 1 |
|---|---|---|---|---|---|---|
| 40° C. | 8 weeks | Residual drug percentage | 99 | 100 | 97 | 93 |
| | | Change of external appearance* | (−) | (−) | (−) | (±) |
| 50° C. | 4 weeks | Residual drug percentage | 97 | 98 | 92 | 85 |
| | | Change of external appearance* | (−) | (−) | (±) | (+) |

*(−): no change in comparison with the external appearance immediately after manufacture (white to yellowish white)
(±): slight change
(+): change to brown color Example 4 and Comparative Example 2

The uncoated tablets obtained in Example 1 and the uncoated tablets obtained in Comparative Example 1 (each 700 tablets) were coated by using a coating machine (Minihighcoater, manufactured by Freund Industries Co., Ltd.) to give film-coated tablets. In the coating procedure, the tablets were coated in aqueous system by use of a coating composition of the following formulation which contains hydroxypropylmethylcellulose and titanium oxide. The coating amount of the coating composition per one tablet was 10 mg.

Formulation of the coating composition

| Formulation of the coating composition | |
|---|---|
| Hydroxypropylmethylcellulose | 510 g |
| Tatanium oxide | 90 g |
| Water | 4950 ml |

The content of phenylpropanolamine and change of the external appearance were evaluated in the same manner as in Example 1. The results are shown in Table 3.

TABLE 3

| Storage temperature | Storage period | | Example 4 | Comparative Example 2 |
|---|---|---|---|---|
| 40° C. | 8 weeks | Residual drug percentage | 99 | 94 |
| | | Change of external appearance* | (−) | (±) |
| 50° C. | 4 weeks | Residual drug percentage | 98 | 87 |
| | | Change of external appearance* | (−) | (+) |

*(−): no change in comparison with the external appearance immediately after manufacture (white)
(±): slight change
(+): change to brown color As is apparent from the results shown in Table 3, the solid pharmaceutical preparation of the present invention is superior in stability of phenylpropanolamine and in external appearance to the preparation of Comparative Example 2.

Example 5

Tablets were prepared in the same manner as in Example 1, except that 953.0 mg of lactose and 218.5 mg of cornstarch in the group I and 2.5 mg of lactose and 111.5 mg of cornstarch in the group P were used. The stability of content of phenylpropanolamine hydrochloride and the change of external appearance were evaluated in the same manner as mentioned and satisfactory results similar to those in Example 1 were obtained.

What is claimed is:

1. A stabilized solid pharmaceutical preparation which comprises ibuprofen and phenylpropanolamine or its hydrochloride as the active ingredients, said preparation being a mixture of a granulated preparation containing ibuprofen and a granulated preparation containing phenylpropanolamine or its hydrochloride with the proviso that the granulated preparation containing phenylpropanolamine or its hydrochloride is (i) substantially free from any reducing sugar, or (ii) contains a reducing sugar in an amount of 5% by weight or less based on the total weight of said granulated preparation containing phenylpropanolamine or its hydrochloride.

2. A stabilized solid pharmaceutical preparation as claimed in claim 1, wherein said granulated preparation of ibuprofen comprises 10 to 60% by weight of ibuprofen, 0 to 10% by weight of other drugs, 0.5 to 15% by weight of a binder, 20 to 85% by weight of an excipient, and 0.5 to 15% by weight of a disintegrator based on the total weight of the preparation of ibuprofen, and said granulated preparation of phenylpropanolamine or its hydrochloride comprises 10 to 60% by weight of phenylpropanolamine or its hydrochloride, 0 to 50% by weight of other drugs, 0.5 to 15% by weight of a binder, 20 to 70% by weight of an excipient, and 0 to 15% by weight of a disintegrator based on the total weight of the preparation of phenylpropanolamine or its hydrochloride.

3. A stabilized solid pharmaceutical preparation as claimed in claim 1, wherein said granulated preparation of ibuprofen comprises 20 to 40% by weight of ibuprofen, 0 to 5% by weight of other drugs, 1 to 10% by weight of a binder, 40 to 75% by weight of an excipient, and 1 to 10% by weight of a disintegrator based on the total weight of the preparation of ibuprofen, and said granulated preparation of phenylpropanolamine or its hydrochloride comprises 20 to 40% by weight of phenylpropanolamine or its hydrochloride, 0 to 40% by weight of other drugs, 1 to 10% by weight of a binder, 30 to 60% by weight of an excipient, and 0 to 10% by weight of a disintegrator based on the total weight of the preparation of phenylpropanolamine or its hydrochloride.

4. A stabilized solid pharmaceutical preparation as claimed in claim 1, wherein in terms of water content, the percentage of loss-on-drying is in the range of 4% by weight or less based on the total weight of the preparation and equilibrium relative humidity is in the range of 33% or less.

5. A stabilized solid pharmaceutical preparation as claimed in claim 1, wherein ibuprofen is contained in a proportion of 5 to 50% by weight and phenylpropanolamine or its hydrochloride is contained in a proportion of 0.1 to 10% by weight, respectively based on the total weight of the preparation.

6. A stabilized solid pharmaceutical preparation as claimed in claim 5, which comprises a granulated preparation containing ibuprofen and a carrier, and a granulated preparation containing phenylpropanolamine or its hydrochloride and a carrier.

7. A stabilized solid pharmaceutical preparation as claimed in claim 1, wherein phenylpropanolamine or its hydrochloride is phenylpropanolamine hydrochloride.

8. A stabilized solid pharmaceutical preparation as claimed in claim 1, wherein said pharmaceutical preparation is a tablet which may be coated.

9. A stabilized solid pharmaceutical preparation as claimed in claim 1, wherein the pharmaceutical preparation is a capsule.

10. A stabilized solid pharmaceutical preparation as claimed in claim 1, wherein said granulated preparation of phenylpropanolamine or its hydrochloride is substantially free from any reducing sugar.

11. A stabilized solid pharmaceutical preparation as claimed in claim 1, wherein said granulated preparation of phenylpropanolamine or its hydrochloride contains a reducing sugar in an amount of 5% by weight or less based on the total weight of said granulated preparation of phenylpropanolamine or its hydrochloride.

12. A stabilized solid pharmaceutical preparation as claimed in claim 11, wherein said reducing sugar is lactose.

13. A method of producing a stabilized solid pharmaceutical preparation containing ibuprofen and phenylpropanolamine or its hydrochloride, which comprises preparing a granulated preparation containing ibuprofen and a granulated preparation containing phenylpropanolamine or its hydrochloride, and mixing hte former with the latter, with the proviso that said preparation of phenylpropanolamine or its hydrochloride (i) is substantially free from any reducing sugar, or (ii) contains a reducing sugar, and the amount of the reducing sugar is 5% by weight or less based on the total weight of said preparation of phenylpropanolamine or its hydrochloride.

14. A method as claimed in claim 13, wherein said granulated preparation of ibuprofen comprises 10 to 60% by weight of ibuprofen, 0 to 10% by weight of other drugs, 0.5 to 15% by weight of a binder, 20 to 85% by weight of an excipient, and 0.5 to 15% by weight of a disintegrator based on the total weight of the preparation of ibuprofen, and said granulated preparation of phenylpropanolamine or its hydrochloride comprises 10 to 60% by weight of phenylpropanolamine or its hydrochloride, 0 to 50% by weight of other drugs, 0.5 to 15% by weight of a binder, 20 to 70% by weight of an excipient, and 0 to 15% by weight of a disintegrator, based on the total weight of the preparation of phenylpropanolamine or its hydrochloride.

15. A method as claimed in claim 13, wherein said granulated preparation of ibuprofen comprises 20 to 40% by weight of ibuprofen, 0 to 5% by weight of other drugs, 1 to 10% by weight of a binder, 40 to 75% by weight of an excipient, and 1 to 10% by weight of a disintegrator based on the total weight of the preparation of ibuprofen, and said granulated preparation of phenylpropanolamine or its hydrochloride comprises 20 to 40% by weight of phenylpropanolamine or its hydrochloride, 0 to 40% by weight of other drugs, 1 to 10% by weight of a binder, 30 to 60% by weight of an excipient, and 0 to 10% by weight of a disintegrator based on the total weight of the preparation of phenylpropanolamine or its hydrochloride.

16. A method of producing a solid pharmaceutical preparation as claimed in claim 13, wherein the granulated preparation containing ibuprofen and the granulated preparation containing phenylpropanolamine or its hydrochloride are mixed in such a proportion as to give said pharmaceutical preparation containing 5 to 50% by weight of ibuprofen and 0.1 to 10% by weight of phenylpropanolamine or its hydrochloride.

17. A method as claimed in claim 13, wherein said granulated preparation of phenylpropanolamine or its hydrochloride is substantially free from any reducing sugar.

18. A method as claimed in claim 13, wherein said granulated preparation of phenylpropanolamine or its hydrochloride contains a reducing sugar in an amount of 5% by weight or less based on the total weight of said granulated preparation of phenylpropanolamine or its hydrochloride.

19. A method as claimed in claim 18, wherein said reducing sugar is lactose.

* * * * *